United States Patent [19]
Kamishita et al.

[11] Patent Number: 6,017,920
[45] Date of Patent: Jan. 25, 2000

[54] ANTIFUNGAL COMPOSITION FOR EXTERNAL USE BEING RETENTIVE IN STRATUM CORNEUM

[75] Inventors: Takuzo Kamishita, Osaka; Takashi Miyazaki, Toyama, both of Japan

[73] Assignee: Toko Yakuhin Kogyo Kabushiki Kaisha, Osaka, Japan

[21] Appl. No.: 08/578,606

[22] PCT Filed: Apr. 19, 1995

[86] PCT No.: PCT/JP95/00773

§ 371 Date: Jan. 5, 1996

§ 102(e) Date: Jan. 5, 1996

[87] PCT Pub. No.: WO95/30440

PCT Pub. Date: Nov. 16, 1995

[30] Foreign Application Priority Data

May 6, 1994 [JP] Japan .................................... 6-094243
Dec. 12, 1994 [JP] Japan .................................... 6-307521

[51] Int. Cl.⁷ .......................... A61K 31/50; A61K 31/415
[52] U.S. Cl. ........................... 514/252; 514/399; 514/912
[58] Field of Search ..................................... 514/252, 399, 514/912

[56] References Cited

U.S. PATENT DOCUMENTS 4,636,520  1/1987  Umio et al. .

FOREIGN PATENT DOCUMENTS 60-61518   4/1985   Japan .
02264723  10/1990   Japan .
2-292219  12/1990   Japan .

OTHER PUBLICATIONS

Chemical Abstract 98:185586 (1982) . Kamishita.

*Primary Examiner*—Zohreh Fay
*Attorney, Agent, or Firm*—Merchant, Gould, Smith, Edell, Welter & Schmidt

[57] ABSTRACT

An antifungal composition for external use being retentive in the stratum corneum containing as an active ingredient an antifungal agent having a high affinity for keratin, wherein the penetration into the stratum corneum of said antifungal agent is enhanced and the retentivity thereof is improved, which comprises incorporating one or more oily liquid substances selected from the group consisting of methyl salicylate, glycol salicylate, crotamiton, and peppermint oil or menthol.

5 Claims, No Drawings

6,017,920

ANTIFUNGAL COMPOSITION FOR EXTERNAL USE BEING RETENTIVE IN STRATUM CORNEUM

TECHNICAL FIELD

The present invention relates to an antifungal composition for external use containing as an active ingredient an antifungal agent having a high affinity for keratin. More particularly, the present invention relates to an antifungal composition for external use being retentive in the stratum corneum, which contains one or more oily liquid substances selected from the group consisting of methyl salicylate, glycol salicylate, crotamiton, and peppermint oil or menthol, in order to enhance the penetration into the stratum corneum of the active antifungal agent having a high affinity for keratin, by which said antifungal agent is more retentive in the stratum corneum.

BACKGROUND ART

In superficial mycosis, fungi invade mainly into the epidermal stratum corneum, and grow therein. Thus, in order to exhibit excellent pharmacological activities in the treatment of superficial mycosis, antifungal agents should stay in a high concentration in the infected epidermal stratum corneum for a prolonged time, in addition to their potent antifungal activity.

Recently, in order to achieve the above purpose, there have been developed and practically used antifungal agents having a high affinity for keratin, which exhibit clinical effects thereof in the treatment of superficial mycosis only by a single application per day. However, in order to obtain a sufficient affinity for the epidermal stratum corneum, antifungal agents should be formulated so that they can penetrate into the epidermal stratum corneum. However, these antifungal agents having a high affinity for keratin are not readily soluble, and it is difficult to increase their solubility when incorporated in the base. As a result, the penetration into the epidermal stratum corneum of these agents is not sufficient so as to form an antifungal composition for external use which is retentive in the stratum corneum using a high affinity for keratin of the active antifungal agent per se at the maximum.

DISCLOSURE OF INVENTION

The present inventors have intensively studied in order to improve the penetration into the stratum corneum of antifungal agents having a high affinity for keratin and the retentivity thereof, and have found that when formulating a composition for external use by incorporating one or more oily liquid substances selected from the group consisting of methyl salicylate, glycol salicylate, crotamiton, and peppermint oil or menthol, the active antifungal agents having a high affinity for keratin show an improved penetration into the stratum corneum as well as an improved retentivity in the stratum corneum, and finally have accomplished the present invention.

More particularly, it has been found that in the preparation of compositions for external use containing as an active ingredient an antifungal agent having a high affinity for keratin, by incorporating with methyl salicylate, glycol salicylate, crotamiton, peppermint oil or menthol, which can dissolve said antifungal agents well and shows a good penetration into the stratum corneum, the penetration into the epidermal stratum corneum of said antifungal agents is enhanced, and further said antifungal agents are more tightly bound to the components of the epidermal stratum corneum, and fixed thereon.

In the composition for external use of the present invention, one or more oily liquid substances selected from the group consisting of methyl salicylate, glycol salicylate, crotamiton, and peppermint oil or menthol can be incorporated thereto by adding and mixing them simultaneously when an antifungal agent having a high affinity for keratin is mixed into a conventional base for external use. Preferably, however, an antifungal agent having a high affinity for keratin is previously dissolved by using various solvents during which the above mentioned oily liquid substances such as methyl salicylate, etc. are added in an amount sufficient for completely dissolving said antifungal agent, and then the resulting solution is incorporated into a conventional base for external use by a conventional method, and the mixture is mixed and formulated by a conventional method. Alternatively, when an antifungal agent can be completely dissolved in the above mentioned oily liquid substance such as methyl salicylate, etc., said antifungal agent is dissolved in these oily liquid substances without using any other solvent, and then the resulting solution is incorporated into a conventional base for external use. Besides, the above oily liquid substances such as methyl salicylate, etc. used in the present invention are expected to show supplemental pharmacological activities as an external agent by themselves and can enhance the activity of the active antifungal agent more. The menthol may be l-menthol, d-menthol and dl-menthol.

The antifungal agent having a high affinity for keratin used in the present invention includes, for example, benzylamine antifungal agents (e.g. butenafine hydrochloride, etc.), imidazole antifungal agents (e.g. bifonazole, neticonazole hydrochloride, ketoconazole, lanoconazole, etc.), allylamine antifungal agents (e.g. terbinafine hydrochloride, etc.), morpholine antifungal agents (e.g. amorolfine hydrochloride, etc.), thiocarbamic acid antifungal agents (e.g. liranaftate, etc.), and the like, which is contained in an amount of 0.5 to 3.0% by weight, preferably in an amount of 1.0 to 2.0% by weight, based on the whole weight of the composition.

The oily liquid substance used in the present antifungal composition for external use being retentive in the stratum corneum, which is selected from the group consisting of methyl salicylate, glycol salicylate, crotamiton, and peppermint oil or menthol, is used in an amount sufficient for completely dissolving an antifungal agent having a high affinity for keratin during the procedure of previously dissolving said antifungal agent by using various solvents, or in an amount sufficient for completely dissolving said antifungal agent in the case of using no solvent, and it is usually used in an amount of 1.0 to 10% by weight based on the whole weight of the composition. Moreover, when it is necessary to use a large amount of an oily liquid substance in order to dissolve an antifungal agent having a high affinity for keratin, or when an antifungal agent cannot completely be dissolved in one oily liquid substance, two or more liquid oily substances may be used.

The antifungal composition for external use being retentive in the stratum corneum of the present invention is formulated in any conventional pharmaceutical preparation for epidermic application, i.e. ointment, cream, gel, gel cream, lotion, solution, etc. These preparations may be prepared by a conventional method by using an active antifungal agent having a high affinity for keratin, said oily liquid substances and various conventional bases for external preparations, but preferably, as mentioned above, an antifungal agent is previously dissolved by using one or more oily liquid substances such as methyl salicylate, etc., or by using said oily liquid substances together with other solvents such as a lower alcohol (e.g. ethanol, etc.), a polyvalent alcohol (e.g. 1,3-butylene glycol, polyethylene glycol 400, etc.), an oily liquid substance (e.g. isopropyl myristate, diisopropyl adipate, octyidodecanol, etc.), a surfactant (e.g. lauromacrogol, polyoxyl 40 stearate, etc.), and the like. The resulting solution is then incorporated into a conventional base for external preparations, and mixed and formulated by a conventional method.

For example, in the preparation of an ointment, vaseline, waxes, paraffins, vegetable oils, plastibase, polyethylene glycol, etc. are used as an external base.

In the preparation of a cream preparation, fats and oils, waxes, higher fatty acids, higher alcohols, fatty acid esters, purified water, polyvalent alcohols, emulsifying agents etc. are used.

In the preparation of a gel preparation, there are used gel bases comprising a carboxyvinyl polymer, a water-soluble basic compound (e.g. alkali metal hydroxides, alkanolamines, etc.), hydroxypropyl cellulose, hydroxypropylmethyl cellulose, polyvinyl alcohol, polyvinylpyrrolidone, purified water, lower alcohols, polyvalent alcohols, polyethylene glycol, and the like.

In the preparation of a gel cream preparation, an emulsifying agent (preferably nonionic surfactants), an oily liquid substance (e.g. liquid paraffin, isopropyl myristate, 2-octyldodecanol, etc.), and the like are used in addition to the above gel bases.

In the preparation of lotion and solution preparations, lower alcohols (e.g. ethanol, isopropanol, etc.) and polyvalent alcohols (e.g. glycerin, propylene glycol, 1,3-butylene glycol, etc.), and purified water are used.

In of the above preparations, any other conventional additives usually incorporated into the epidermic preparations, such as antioxidants, preservatives, humectants, chelating agents, and the like, may also be incorporated. Those preparations may be prepared under the conventional conditions for the conventional epidermic preparations.

BEST MODE FOR CARRYING OUT THE INVENTION

The composition of the present invention is illustrated in more detail by the following Examples.

EXAMPLE 1 (Ointment)

An ointment is prepared by the following formulation.

| (Components) | (Amount) |
| --- | --- |
| Bifonazole | 1.0 |
| Glycol salicylate | 3.0 |
| Cetostearyl alcohol | 5.0 |
| White vaseline | 91.0 |
| Totally | 100.0 g |

Cetostearyl alcohol and white vaseline are dissolved by warming on a water bath, and thereto is added a solution of bifonazole in glycol salicylate which is prepared by warming at about 70 to 80° C., and the mixture is well stirred and, thereafter, cooled and kneaded until it becomes semisolid to give an ointment.

EXAMPLE 2 (Ointment)

An ointment is prepared by the following formulation.

| (Components) | (Amount) |
| --- | --- |
| Ketoconazole | 0.5 |
| Crotamiton | 5.0 |
| Glycol salicylate | 3.0 |
| Plastibase | 91.5 |
| Totally | 100.0 g |

To plastibase is added a solution of ketoconazole in crotamiton and glycol salicylate which is prepared by warming at about 70 to 80° C., and the mixture is well stirred and kneaded to give an ointment.

EXAMPLE 3 (Ointment)

An ointment is prepared by the following formulation.

| (Components) | (Amount) |
| --- | --- |
| Lanoconazole | 2.0 |
| Crotamiton | 5.0 |
| Polyethylene glycol 400 | 40.0 |
| Polyethylene glycol 4000 | 53.0 |
| Totally | 100.0 g |

Polyethylene glycol 4000 is dissolved by warming on a water bath and thereto is added a solution of lanoconazole in crotamiton and polyethylene glycol 400, which is prepared by warming at about 70 to 80° C., and the mixture is well stirred and, thereafter, cooled and kneaded until it becomes semisolid to give an ointment.

EXAMPLE 4 (Ointment)

An ointment is prepared by the following formulation.

| (Components) | (Amount) |
| --- | --- |
| Bifonazole | 2.0 |
| Peppermint oil | 5.0 |
| Isopropyl myristate | 5.0 |
| Glycerin monostearate | 3.0 |
| White vaseline | 85.0 |
| Totally | 100.0 g |

White vaseline is dissolved by warming on a water bath and thereto is added a solution of bifonazole in peppermint oil, isopropyl myristate and glycerin monostearate, which is prepared by warming at about 70 to 80° C., and the mixture is well stirred and, thereafter, cooled and kneaded until it becomes semisolid to give an ointment.

EXAMPLE 5 (Ointment)

An ointment is prepared by the following formulation.

| (Components) | (Amount) |
| --- | --- |
| Bifonazole | 0.5 |
| Glycol salicylate | 5.0 |
| l-Menthol | 2.0 |

-continued

| (Components) | (Amount) |
|---|---|
| Lauromacrogol | 2.5 |
| White vaseline | 90.0 |
| Totally | 100.0 g |

White vaseline is dissolved by warming on a water bath and thereto is added a solution of bifonazole in glycol salicylate, l-menthol and lauromacrogol, which is prepared by warming at about 70 to 80° C., and the mixture is well stirred and, thereafter, cooled and kneaded until it becomes semisolid to give an ointment.

EXAMPLE 6 (Ointment)

An ointment is prepared by the following formulation.

| (Components) | (Amount) |
|---|---|
| Terbinafine hydrochloride | 1.0 |
| Crotamiton | 10.0 |
| 2% Aqueous sodium hydroxide solution | 10.0 |
| Sorbitan sesqui-oleate | 6.0 |
| Octyldodecanol | 5.0 |
| White vaseline | 68.0 |
| Totally | 100.0 g |

White vaseline is dissolved by warming on a water bath and thereto is added a solution of terbinafine hydrochloride in crotamiton, 2% aqueous sodium hydroxide solution, sorbitan sesqui-oleate and octyldodecanol, which is prepared by warming at about 70 to 80° C., and the mixture is well stirred and, thereafter, cooled and kneaded until it becomes semisolid to give an ointment.

EXAMPLE 7 (Cream preparation)

A cream preparation is prepared by the following formulation.

| (Components) | (Amount) |
|---|---|
| Butenatine hydrochloride | 0.5 |
| Glycol salicylate | 2.0 |
| Peppermint oil | 1.0 |
| 2% Aqueous sodium hydroxide solution | 3.0 |
| White vaseline | 25.0 |
| Stearyl alcohol | 15.0 |
| Propylene glycol | 10.0 |
| Sodium laurylsulfate | 1.5 |
| Lauromacrogol | 2.0 |
| Ethyl parahydroxybenzoate | 0.025 |
| Butyl parahydroxybenzoate | 0.015 |
| Purified water | 39.96 |
| Totally | 100.0 g |

Butenafine hydrochloride is dissolved in glycol salicylate, peppermint oil, a 2% aqueous sodium hydroxide solution and lauromacrogol by warming at about 70 to 80° C. Thereto are added white vaseline, stearyl alcohol, and butyl parahydroxybenzoate, and the mixture is dissolved and well stirred on a water bath and kept at about 70 to 80° C. on a water bath. To the mixture is added a solution of other components which is previously prepared by dissolving them in purified water and warming at about 70 to 80° C. The mixture is well mixed and stirred until it becomes semisolid to give a cream preparation.

EXAMPLE 8 (Cream preparation)

A cream preparation is prepared by the following formulation.

| (Components) | (Amount) |
|---|---|
| Lanoconazole | 1.0 |
| Crotamiton | 10.0 |
| l-Menthol | 2.0 |
| 2% Aqueous sodium hydroxide solution | 10.0 |
| White vaseline | 10.0 |
| Cetanol | 5.0 |
| Stearyl alcohol | 15.0 |
| Propylene glycol | 10.0 |
| Sodium laurylsulfate | 1.0 |
| Lauromacrogol | 2.0 |
| Ethyl parahydroxybenzoate | 0.025 |
| Butyl parahydroxybenzoate | 0.015 |
| Purified water | 33.96 |
| Totally | 100.0 g |

Lanoconazole is dissolved in crotamiton, l-menthol, a 2% aqueous sodium hydroxide solution and lauromacrogol by warming at about 70 to 80° C. Thereto are added white vaseline, cetanol, stearyl alcohol and butyl parahydroxybenzoate, and the mixture is dissolved by warming and well stirred on a water bath and kept at about 70 to 80° C. on a water bath. To the mixture is added a solution of other components which is previously prepared by dissolving them in purified water and warming at about 70 to 80° C. The mixture is well mixed and stirred until it becomes semisolid to give a cream preparation.

EXAMPLE 9 (Cream preparation)

A cream preparation is prepared by the following formulation.

| (Components) | (Amount) |
|---|---|
| Amorolfine hydrochloride | 1.0 |
| Crotamiton | 5.0 |
| Methyl salicylate | 2.0 |
| Diisopropyl adipate | 10.0 |
| 2% Aqueous sodium hydroxide solution | 5.0 |
| Lipophilic glycerin monooleate | 5.0 |
| Plastibase | 72.0 |
| Totally | 100.0 g |

Amorolfine hydrochloride is dissolved in crotamiton, methyl salicylate, diisopropyl adipate, a 2% aqueous sodium hydroxide solution and lipophilic glycerin monooleate by warming at about 70 to 80° C., and thereto is added plastibase. The mixture is well mixed and stirred until it becomes homogenous to give a cream preparation.

EXAMPLE 10 (Cream preparation)

A cream preparation is prepared by the following formulation.

| (Components) | (Amount) |
|---|---|
| Liranaftate | 1.0 |
| Crotamiton | 10.0 |
| Peppermint oil | 3.0 |
| Diisopropyl adipate | 5.0 |

| (Components) | (Amount) |
|---|---|
| White vaseline | 25.0 |
| Stearyl alcohol | 25.0 |
| 1,3-Butylene glycol | 5.0 |
| Sorbitan sesqui-oleate | 2.0 |
| Polyoxyl 40 stearate | 5.0 |
| Methyl parahydroxybenzoate | 0.025 |
| Propyl parahydroxybenzoate | 0.015 |
| Purified water | 18.96 |
| Totally | 100.0 g |

Liranaftate is dissolved in crotamiton, peppermint oil, diisopropyl adipate, sorbitan sesqui-oleate and polyoxyl 40 stearate by warming at about 70 to 80° C., and thereto are added white vaseline, stearyl alcohol, and propyl parahydroxybenzoate. The mixture is well dissolved and stirred by warming on a water bath, and kept at about 70 to 80° C. To the mixture is added a solution of the other components, which is previously prepared by dissolving them in purified water and warmed at about 70 to 80° C., and the mixture is well mixed and stirred until it becomes semisolid to give a cream preparation.

EXAMPLE 11 (Gel preparation)

A gel preparation is prepared by the following formulation.

| (Components) | (Amount) |
|---|---|
| Bifonazole | 0.5 |
| Crotamiton | 1.0 |
| Denatured alcohol | 66.5 |
| Hydroxypropylmethyl cellulose | 0.5 |
| 1,3-Butylene glycol | 5.0 |
| 4% Aqueous carboxyvinyl polymer solution | 25.0 |
| Diisopropanolamine | 1.5 |
| Totally | 100.0 g |

Bifonazole is dissolved in a mixture of crotamiton, a part of denatured alcohol and 1,3-butylene glycol by stirring well. Separately, to a homogeneous mixture of hydroxypropylmethyl cellulose in a part of denatured alcohol is added a 4% aqueous carboxyvinyl polymer solution and stirred. Thereto is added diisopropanolamine, and the mixture is made homogeneous by stirring to give a gel base. To the gel base is added the above bifonazole-containing solution, and the mixture is homogeneously stirred to give a gel preparation.

EXAMPLE 12 (Gel preparation)

A gel preparation is prepared by the following formulation.

| (Components) | (Amount) |
|---|---|
| Neticonazole hydrochloride | 1.0 |
| Crotamiton | 5.0 |
| Methyl salicylate | 2.0 |
| Denatured alcohol | 60.4 |
| Hydroxypropylmethyl cellulose | 1.0 |
| 1,3-Butylene glycol | 5.0 |
| 4% Aqueous carboxyvinyl polymer solution | 25.0 |
| Diisopropanolamine | 0.6 |
| Totally | 100.0 g |

Neticonazole hydrochloride is dissolved in a mixture of crotamiton, methyl salicylate, a part of denatured alcohol and 1,3-butylene glycol by stirring well. Separately, to a homogeneous mixture of hydroxypropylmethyl cellulose in a part of denatured alcohol is added a 4% aqueous carboxyvinyl polymer solution and stirred, and thereto is added diisopropanolamine, and the mixture is made homogeneous by stirring to give a gel base. To the gel base is added the above neticonazole hydrochloride-containing solution, and the mixture is homogeneously stirred to give a gel preparation.

EXAMPLE 13 (Gel preparation)

A gel preparation is prepared by the following formulation.

| (Components) | (Amount) |
|---|---|
| Terbinafine hydrochloride | 3.0 |
| Crotamiton | 10.0 |
| Denatured alcohol | 50.5 |
| Hydroxypropylmethyl cellulose | 1.0 |
| Polyethylene glycol 400 | 10.0 |
| 4% Aqueous carboxyvinyl polymer solution | 25.0 |
| Diisopropanolamine | 0.5 |
| Totally | 100.0 g |

Terbinafine hydrochloride is dissolved in a mixture of crotamiton, a part of denatured alcohol and polyethylene glycol 400 with stirring well. Separately, to a homogeneous mixture of hydroxypropylmethyl cellulose in a part of denatured alcohol is added a 4% aqueous carboxyvinyl polymer solution and stirred, and thereto is added diisopropanolamine, and the mixture is made homogeneous by stirring to give a gel base. To the gel base is added the above terbinafine hydrochloride-containing solution, and the mixture is homogeneously stirred to give a gel preparation.

EXAMPLE 14 (Gel preparation)

A gel preparation is prepared by the following formulation.

| (Components) | (Amount) |
|---|---|
| Bifonazole | 1.0 |
| l-Menthol | 3.0 |
| Denatured alcohol | 64.0 |
| Hydroxypropylmethyl cellulose | 0.5 |
| 1,3-Butylene glycol | 5.0 |
| 4% Aqueous carboxyvinyl polymer solution | 25.0 |
| Diisopropanolamine | 1.5 |
| Totally | 100.0 g |

Bifonazole is dissolved in a mixture of l-menthol, a part of denatured alcohol and 1,3-butylene glycol with stirring well. Separately, to a homogeneous mixture of hydroxypropylmethyl cellulose in a part of denatured alcohol is added a 4% aqueous carboxyvinyl polymer solution and stirred, and thereto is added diisopropanolamine, and the mixture is made homogeneous by stirring to give a gel base. To the gel base is added the above bifonazole-containing solution, and the mixture is homogeneously stirred to give a gel preparation.

EXAMPLE 15 (Gel cream preparation)

A gel cream preparation is prepared by the following formulation.

| (Components) | (Amount) |
|---|---|
| Bifonazole | 1.0 |
| Crotamiton | 3.0 |
| Peppermint oil | 1.0 |
| Octyldodecanol | 10.0 |
| Glycerin monostearate | 0.5 |
| Polyethyleneglycol monostearate (45E.O.) | 0.5 |
| 1,3-Butylene glycol | 5.0 |
| 4% Aqueous carboxyvinyl polymer solution | 30.0 |
| 2% Aqueous sodium hydroxide solution | 27.5 |
| Purified water | 21.5 |
| Totally | 100.0 g |

Bifonazole is dissolved in a mixture of crotamiton, peppermint oil, octyldodecanol, glycerin monostearate and polyethyleneglycol monostearate (45E.O.) by warming at about 70 to 80° C. Separately, to a 4% aqueous carboxyvinyl polymer solution are added a 2% aqueous sodium hydroxide solution, 1,3-butylene glycol and purified water and the mixture is made homogenous by stirring to give a gel substrate, and warmed to about 70 to 80° C. To the gel substrate is added the above active ingredient-containing solution, and emulsified, and mixed homogeneously to give a gel cream preparation.

EXAMPLE 16 (Gel cream preparation)

A gel cream preparation is prepared by the following formulation.

| (Components) | (Amount) |
|---|---|
| Ketoconazole | 2.0 |
| Glycol salicylate | 10.0 |
| Crotamiton | 5.0 |
| Peppermint oil | 3.0 |
| Diisopropyl adipate | 15.0 |
| Glycerin monostearate | 2.0 |
| Polyoxyl 40 monostearate | 2.0 |
| 1,3-Butylene glycol | 5.0 |
| 4% Aqueous carboxyvinyl polymer solution | 25.0 |
| 2% Aqueous sodium hydroxide solution | 10.0 |
| Purified water | 21.0 |
| Totally | 100.0 g |

Ketoconazole is dissolved in a mixture of glycol salicylate, crotamiton, peppermint oil, diisopropyl adipate, glycerin monostearate and polyoxyl 40 monostearate by warming at about 70 to 80° C. Separately, to a 4% aqueous carboxyvinyl polymer solution are added a 2% aqueous sodium hydroxide solution, 1,3-butylene glycol and purified water and the mixture is made homogenous by stirring to give a gel substrate, and warmed to about 70 to 80° C. To the gel substrate thus obtained is added the above active ingredient-containing solution, and emulsified, and mixed homogeneously to give a gel cream preparation.

REFERENCE EXAMPLE 1 (Gel cream preparation)

A gel cream preparation is prepared by the same components as those of the above Example 16 except for glycol salicylate, crotamiton and peppermint oil, in the same manner as in Example 16.

| (Components) | (Amount) |
|---|---|
| Ketoconazole | 2.0 |
| Diisopropyl adipate | 15.0 |
| Glycerin monostearate | 2.0 |
| Polyoxyl 40 monostearate | 2.0 |
| 1,3-Butylene glycol | 5.0 |
| 4% Aqueous carboxyvinyl polymer solution | 25.0 |
| 2% Aqueous sodium hydroxide solution | 10.0 |
| Purified water | 39.0 |
| Totally | 100.0 g |

EXAMPLE 17 (Gel cream preparation)

A gel cream preparation is prepared by the following formulation.

| (Components) | (Amount) |
|---|---|
| Terbinatine hydrochloride | 1.0 |
| Crotamiton | 5.0 |
| Isopropyl myristate | 10.0 |
| Lauromacrogol | 2.0 |
| 1,3-Butylene glycol | 5.0 |
| 4% Aqueous carboxyvinyl polymer solution | 30.0 |
| 2% Aqueous sodium hydroxide solution | 35.0 |
| Purified water | 12.0 |
| Totally | 100.0 g |

Terbinafine hydrochloride is dissolved in a mixture of crotamiton, diisopropyl myristate, lauromacrogol and a 2% aqueous sodium hydroxide solution by warming at about 70 to 80° C. Separately, to a 4% aqueous carboxyvinyl polymer solution are added the remaining 2% aqueous sodium hydroxide solution, 1,3-butylene glycol and purified water and the mixture is made homogenous by stirring to give a gel substrate, and warmed to about 70 to 80° C. To the gel substrate thus obtained is added the above active ingredient-containing solution, and emulsified, and mixed homogeneously to give a gel cream preparation.

EXAMPLE 18 (Gel cream preparation)

A gel cream preparation is prepared by the following formulation.

| (Components) | (Amount) |
|---|---|
| Lanoconazole | 1.0 |
| l-Menthol | 3.0 |
| Diisopropyl adipate | 10.0 |
| Octyldodecanol | 10.0 |
| Glycerin monostearate | 2.5 |
| Polyoxyl 40 monostearate | 2.5 |
| 1,3-Butylene glycol | 10.0 |
| 4% Aqueous carboxyvinyl polymer solution | 25.0 |
| 2% Aqueous sodium hydroxide solution | 20.0 |
| Purified water | 16.0 |
| Totally | 100.0 g |

Lanoconazole is dissolved in a mixture of l-menthol, diisopropyl adipate, octyldodecanol, glycerin monostearate and polyoxyl 40 monostearate by warming at about 70 to 80° C. Separately, to a 4% aqueous carboxyvinyl polymer solution are added a 2% aqueous sodium hydroxide solution, 1,3-butylene glycol and purified water and the mixture is made homogenous by stirring to give a gel substrate, and warmed to about 70 to 80° C. To the gel substrate thus obtained is added the above active ingredient-containing solution, and emulsified, and mixed homogeneously to give a gel cream preparation.

EXAMPLE 19 (Solution preparation)

A solution preparation is prepared by the following formulation.

| (Components) | (Amount) |
| --- | --- |
| Bifonazole | 1.0 |
| Peppermint oil | 5.0 |
| Polyethylene glycol 400 | q.s. |
| Totally | 100.0 ml |

Bifonazole is dissolved in peppermint oil by warming at about 70 to 80° C. To the mixture is added polyethylene glycol 400, and the mixture is made homogenous by stirring. The total volume thereof is adjusted to 100 ml, and the mixture is filtered to give a solution preparation.

EXAMPLE 20 (Solution preparation)

A solution preparation is prepared by the following formulation.

| (Components) | (Amount) |
| --- | --- |
| Bifonazole | 1.0 |
| Crotamiton | 5.0 |
| Polyethylene glycol 400 | 10.0 |
| Purified water | 20.0 |
| Denatured alcohol | q.s. |
| Totally | 100.0 ml |

Bifonazole is dissolved in a mixture of crotamiton and polyethylene glycol 400 by warming at about 70 to 80° C. To the mixture is added purified water, and thereto is further added denatured alcohol, and the mixture is made homogenous by stirring. The total volume thereof is adjusted to 100 ml, and the mixture is filtered to give a solution preparation.

REFERENCE EXAMPLE 2 (Solution preparation)

A solution preparation is prepared by the same components as those of Example 20 except for crotamiton, in the same manner as Example 20.

| (Components) | (Amount) |
| --- | --- |
| Bifonazole | 1.0 |
| Polyethylene glycol 400 | 10.0 |
| Purified water | 20.0 |
| Denatured alcohol | q.s. |
| Totally | 100.0 ml |

EXAMPLE 21 (Solution preparation)

A solution preparation is prepared by the following formulation.

| (Components) | (Amount) |
| --- | --- |
| Neticonazole hydrochloride | 3.0 |
| Crotamiton | 5.0 |
| Methyl salicylate | 1.0 |
| Methyl ethyl ketone | 20.0 |
| Propylene glycol | 10.0 |
| Denatured alcohol | q.s. |
| Totally | 100.0 ml |

Neticonazole hydrochloride is dissolved in a mixture of crotamiton, methyl salicylate and methyl ethyl ketone. To the mixture are added propylene glycol and denatured alcohol, and the mixture is made homogenous by stirring. The total volume of the mixture is adjusted to 100 ml, and the mixture is filtered to give a solution preparation.

EXAMPLE 22 (Solution preparation)

A solution preparation is prepared by the following formulation.

| (Components) | (Amount) |
| --- | --- |
| Terbinafine hydrochloride | 1.0 |
| Glycol salicylate | 5.0 |
| Denatured alcohol | 60.0 |
| 1,3-Butylene glycol | 20.0 |
| Purified water | q.s. |
| Totally | 100.0 ml |

Terbinafine hydrochloride is dissolved in a mixture of glycol salicylate and a part of denatured alcohol, and thereto are added purified alcohol and 1,3-butylene glycol, and further thereto is added the remaining denatured alcohol. The mixture is made homogenous by stirring, and the total volume thereof is adjusted to 100 ml. The mixture is filtered to give a solution preparation.

EXAMPLE 23 (Solution preparation)

A solution preparation is prepared by the following formulation.

| (Components) | (Amount) |
| --- | --- |
| Liranaftate | 0.5 |
| Methyl salicylate | 2.5 |
| Diethyl sebacate | 5.0 |
| Purified water | 10.0 |
| Denatured alcohol | q.s. |
| Totally | 100.0 ml |

Liranaftate is dissolved in a mixture of methyl salicylate, diethyl sebacate and a part of denatured alcohol, and thereto is added purified water, and further added the remaining denatured alcohol. The mixture is made homogeneous by stirring, and the total volume thereof is adjusted to 100 ml, and the mixture is filtered to give a solution preparation.

Experiment 1

Penetration test into the stratum corneum of antifungal agents:

The penetration into the stratum corneum was tested on the gel cream preparation of the above Example 16 (referred to as Gel cream preparation A), the gel cream preparation of Reference Example 1 (referred to as Gel cream preparation B), the solution preparation of Example 20 (referred to as Solution preparation A) and the solution preparation of Reference Example 2 (referred to as Solution preparation B) in the following manner.

Method:

A test preparation was applied to an area of 5×5 cm at the inside of human upper arm at a dose of each 10 ml or 10 g, and allowed to stand for 6 hours. The test composition remaining at the applied site was wiped off by an absorbent cotton soaked with 70% aqueous ethanol solution. Subsequently, a cellophane tape was applied to the surface of the skin at the same area and pushed thereon, and tore off to have the stratum corneum peeled. These procedures by the cellophane tape were repeated ten times using a new cellophane tape every time, and the stratum corneum was completely peeled off. The cellophane tapes thus obtained were collected, and extracted with ethanol. The amount of bifonazole or ketoconazole (active antifungal agent in a test composition) in the stratum corneum was determined by high performance liquid chromatography.

Results: The results are shown in Table 1.

TABLE 1

| Test preparation | Amount of ketoconazole in the stratum corneum (µg) | Amount of bifonazole in the stratum corneum (µg) |
|---|---|---|
| Gel cream preparation A (Ex. 16) | 18.13 | — |
| Gel cream preparation B (Ref. Ex. 1) | 1.05 | — |
| Solution preparation A (Ex. 20) | — | 14.23 |
| Solution preparation B (Ref. Ex. 2) | — | 8.48 |

We claim:

1. An anti-fungal composition comprising an anti-fungal effective amount of an anti-fungal agent having a high affinity for keratin selected from the group consisting of butenafine hydrochloride, bifonazole, neticonazole hydrochloride, ketoconazole, lanoconazole, terbinafine hydrochloride, amorolfine hydrochloride and liranaftate, and a suitable carrier for topical application, the composition further comprising, crotamiton, the composition being retentive in the stratum corneum of a subject to which the composition has been applied topically.

2. The antifungal composition for external use being retentive in the stratum corneum according to claim 1, wherein the antifungal agent having a high affinity for keratin is contained in an amount of 0.5 to 3.0% by weight based on the whole weight of the composition.

3. The antifungal composition for external use being retentive in the stratum corneum according to claim 1, wherein crotamiton is contained in an amount of 1 to 10% by weight based on the whole weight of the composition.

4. The antifungal composition for external use being retentive in the stratum corneum according to claim 1, which is in the form of an ointment, a cream preparation, a gel preparation, a gel cream preparation or a solution preparation.

5. A method of providing a topical anti-fungal effect to a subject in need thereof, comprising topically administering to the subject the composition of claim 1, the anti-fungal agent being retained in the stratum corneum after application of the composition to the subject.

* * * * *